United States Patent
Saslawski et al.

(10) Patent No.: US 6,426,087 B1
(45) Date of Patent: Jul. 30, 2002

(54) ORALLY ADMINISTRABLE IMMEDIATE-RELEASE AND PROLONGED-RELEASE GALENIC FORM COMPRISING AN ABSORPTION-PROMOTING AGENT AND USE OF THIS ABSORPTION-PROMOTING AGENT

(75) Inventors: Olivier Saslawski; Philippe Giet; Dominique Michel; Thierry Holot, all of Lyons (FR)

(73) Assignee: Merck Patent Gesellschaft mit, Darmstadt (DE)

( * ) Notice: Subject to any disclaimer, the term of this patent is extended or adjusted under 35 U.S.C. 154(b) by 0 days.

(21) Appl. No.: 09/622,663

(22) PCT Filed: Feb. 16, 1999

(86) PCT No.: PCT/EP99/00994

§ 371 (c)(1),
(2), (4) Date: Aug. 22, 2000

(87) PCT Pub. No.: WO99/42086

PCT Pub. Date: Aug. 26, 1999

(30) Foreign Application Priority Data

Feb. 23, 1998 (DE) .......................................... 98 02 143

(51) Int. Cl.$^7$ ............................................... A61K 9/127
(52) U.S. Cl. ...................... 424/450; 424/456; 424/460; 424/464; 424/488; 424/489; 424/490; 424/498; 424/499
(58) Field of Search ................................ 424/400, 464, 424/450, 456, 489, 490, 448, 449, 488

(56) References Cited

U.S. PATENT DOCUMENTS

| | | | |
|---|---|---|---|
| 5,139,786 A | * | 8/1992 | Ferrine et al. |
| 5,190,748 A | | 3/1993 | Bachynsky et al. |
| 5,858,398 A | * | 1/1999 | Cho ............................ 424/450 |

FOREIGN PATENT DOCUMENTS

| | | | |
|---|---|---|---|
| EP | 223369 | * | 5/1987 |
| FR | 2 457 281 | | 12/1980 |
| JP | 62265226 | * | 11/1987 |
| JP | 3275633 | * | 6/1991 |
| WO | WO 97/05903 | | 2/1997 |

OTHER PUBLICATIONS

Swenson et al., "Intestinal permeability enhancement; efficacy, acute local toxicity and reversibility" Pharm. Res., vol. 11, No. 8, 1994, pp. 1132–1142.
Van Hoogdalem E.J., et al., "Intestinal drug absorption enhacement: an overview" Pharm. Ther., vol. 44, 1989, pp. 404–443.
Aungst B. et al., "Enhancement of the intestinal absorption of peptides and non peptides", J. of Controlled Release, vol. 41, 1996, pp. 19–31.
Patent Abstracts of Japan, vol. 012, No. 148 (C–493) May 7, 1988 & JP 62 265226 (Fujisawa Pharmaceut. Co., Ltd.), Nov. 18, 1987.
Database WPI, Section Ch., Week 8801, Derwent Publications Ltd., London, GB; Class B01, AN 88–002672 & JP 62 265226 (Fujisawa Pharmaceut. Co., Ltd.).
Patent Abstracts of Japan, Vo. 016, No. 093 (C–0917), Mar. 6, 1992 & JP 03 275633 Teikoku Seiyaku KK), Dec. 6, 1991.
Database WPI, Section Ch., Week 9204, Derwent Publications Ltd., London, GB, Class A12, AN 92–028863 & JP 03 275633 (Teikoku Seiyaku KK).
Swenson E. Et Al: "Intestinal permeability enhancement: efficacy, acute local toxicity and reversibility" Pharm. Res., vol. 11, No. 8, 1994.*
Van Hoogdalem E.J. Et Al: "Intestinal drug absorption enhancement: an overview" Pharm. Ther., vol. 44, 1989, pp. 404–443, XP002086283.*
Aungst B. Et Al: "Enhancement of the intestinal absorption of peptides and non peptides" J. of Controlled Release, vol. 41,—1996 p. 19–31 XP002086284.*
Patent Abstracts of Japan vol. 012, No. 148 (C–493), May 7, 1988 & JP 62 265226 A (Fujisawa Pharmaceut Co Ltd), Nov. 18, 1987 & Database WPI Section Ch, Week 8801 Derwent Publications Ltd., London, GB; Class B01, AN.*
Patent Abstracts of Japan vol. 016, No. 093 (C–0917), Mar. 6, 1992 & JP 03 275633 A (Teikoku Seiyaku KK), Dec. 6, 1991 & Database WPI Section Ch, Week 9204 Derwent Publications Ltd., London, GB; Class A12, AN 92–028863 & JP 03 275633 A (Teikoku Seiyaku KK).*

* cited by examiner

Primary Examiner—Deborah D Carr
(74) Attorney, Agent, or Firm—Millen, White, Zelano & Branigan, P.C.

(57) ABSTRACT

The present invention relates to an orally administrable galenic form allowing improved absorption by the transmembrane or paracellular route in the gastrointestinal tract of active ingredients which are hydrophilic or ionizable in physiol. media, comprising at least one such active ingredient, an absorption-promoting agent having an HLB>8, the the absorption-promoting agent consisting of one or more lipid substances chosen from: polysorbates; polyoxyethylene ethers; esters of polyoxyethylene and fatty acids; fatty acids; fatty alcs.; bile acids and their salts with pharmaceutically acceptable cations; esters of C1–C6 alkanol with fatty acids; esters of polyol with fatty acids, the polyol comprising from 2 to 6 hydroxyl functional groups; and polyglycolyzed glycerides; in combination with one or more pharmaceutically acceptable excipients, the pharmaceutical forms comprising captopril being excluded. A controlled-release tablet contained (1) cores contg. calcium acamprosate 50, Gelucire 44/14 10, Compritol 10, microcryst. cellulose 19, Povidone 10, and Mg stearate 1% and (2) a film-coating compn. contg. HPMC 64, PEG-4000 15, and talc 21%.

28 Claims, 7 Drawing Sheets

Figure 1:
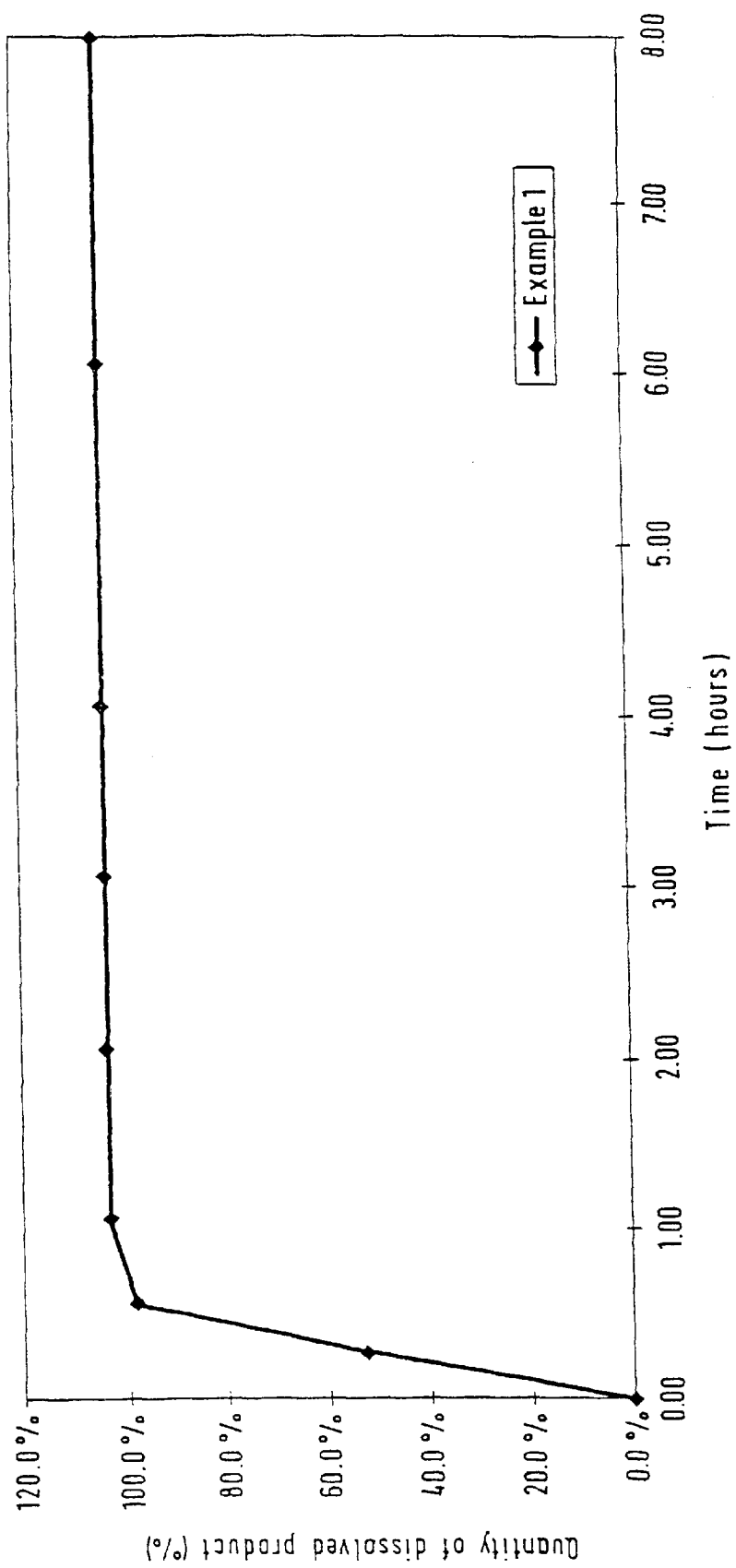
Figure 2:
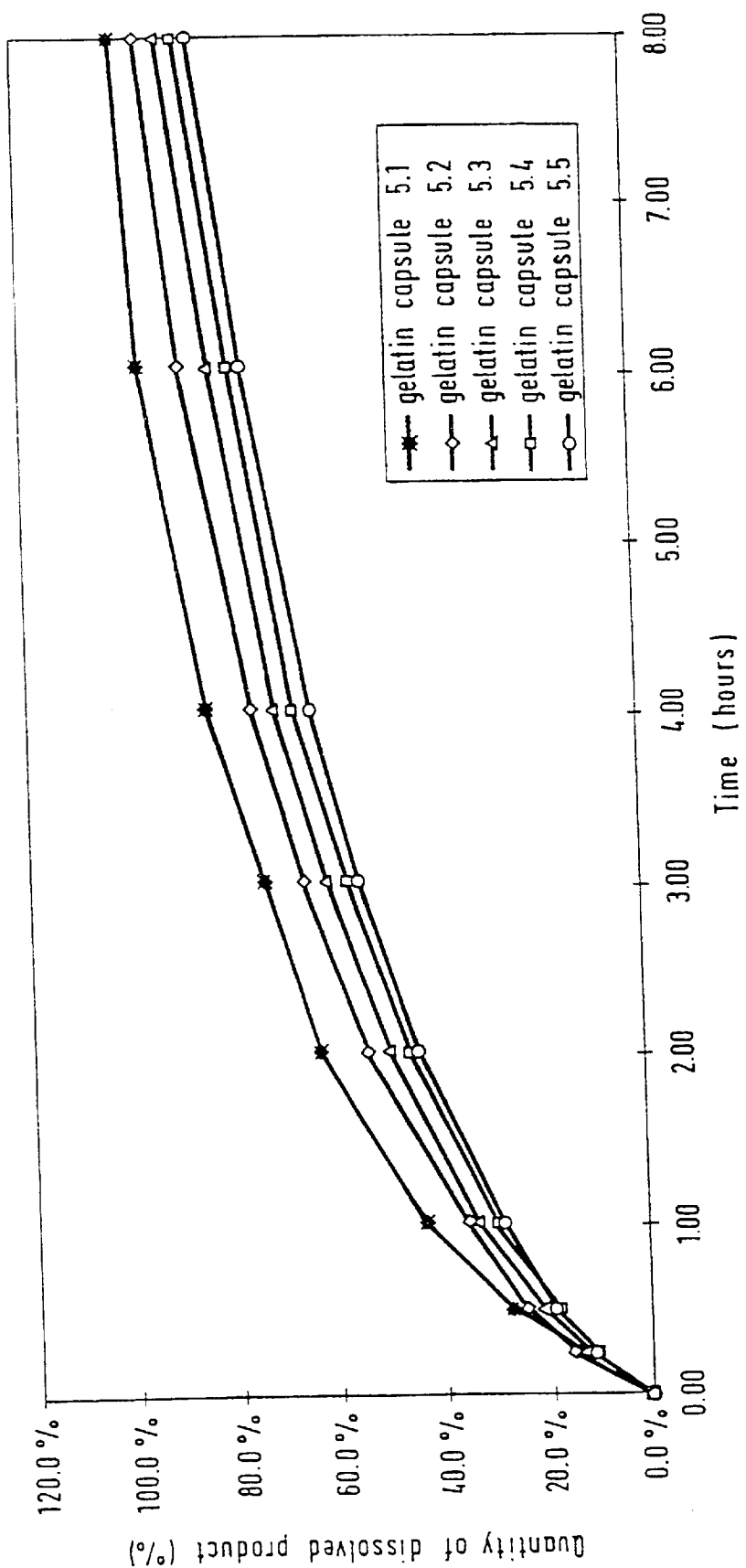

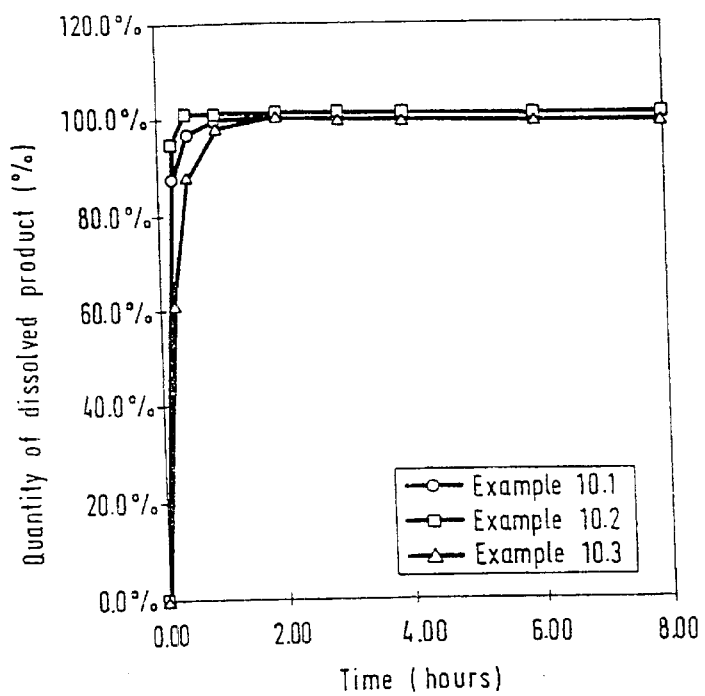
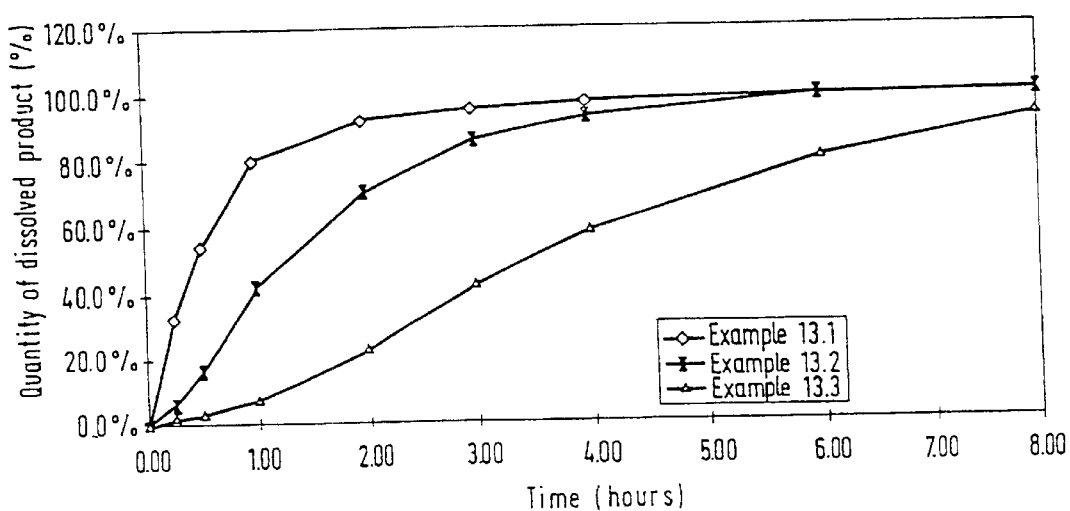

ORALLY ADMINISTRABLE IMMEDIATE-RELEASE AND PROLONGED-RELEASE GALENIC FORM COMPRISING AN ABSORPTION-PROMOTING AGENT AND USE OF THIS ABSORPTION-PROMOTING AGENT

This application is a 371 of PCT/EP99/00994 filed Feb. 16,1999.

The invention relates to orally administrable galenic forms comprising one or more active ingredients which are hydrophilic or ionizable in physiological media in combination with one or more excipients. These galenic forms are preferably solid forms such as tablets or gelatin capsules. The galenic compositions of the invention are particularly advantageous in that they allow improved absorption of active ingredients which are hydrophilic and/or ionizable in physiological media, by the transmembrane or paracellular route, because of their particular excipient composition.

The absorption of orally administered active ingredients essentially takes place by the transmembrane or paracellular route at the level of the mucous membranes of the gastrointestinal tract. In the case of active ingredients which are hydrophilic or ionizable in physiological media, the absorption predominantly takes place by the paracellular route. Because of this, the bioavailability of this type of active ingredient is very low, the kinetics of absorption being very slow. Numerous authors have more precisely studied the kinetics of absorption of active ingredients in the form of calcium salts and have observed that the transport of these substances by the paracellular route is very limited: it appears that the calcium salts have the effect of closing again the channels present between the cells which provide for transport by the paracellular route. Reference may be made, for example, to P. Artursson and C. Magnusson, J. Pharm. Sci., 79, 595, 1990 and S. G. Milton and V. P. Knutson, J. Cell. Physiol., 144, 498, 1990.

The use of various excipient systems comprising liquid or amphiphilic compounds such as semisynthetic glycerides for promoting the absorption of active substances has been abundantly illustrated in the art. In this regard, there may be mentioned the following state of the art documents: WO 93/00891, EP 670 166, WO 95/08 983, WO 94/23 733 and WO 96/21 439. All the prior art formulations are intended, however, to improve the bioavailability of lipophilic active substances. Moreover, the formulations provided in the case of tablets, granules or microgranules do not always allow control of the kinetics of release.

This may result in an intense increase in the plasma concentration, which is quite often followed, in the case of compounds having a short half-life, by a rapid decrease in these levels which reach values below the therapeutic threshold. Multiplication of the number of doses is then necessary in order to maintain a therapeutic effect for the medication.

However, control of the absorption of the active ingredients at the level of the gastrointestinal tract will ensure the efficacy of the therapy used. Furthermore, modulation of the release (while preserving an optimized absorption) makes it possible to ensure better therapeutic cover and to improve tolerance and compliance. Thus, it is possible to reduce the number of doses of the medicament and to thereby ensure compliance with the treatment. This is essential in the case of treatment of long-term, or even chronic, disorders or pathologies.

The galenic forms of the invention allow improvement in the absorption of the active ingredients which are hydrophilic and/or ionizable in physiological media, the control of the kinetics of release and the maintenance of the yield of absorption, this being also in the case of solid pharmaceutical forms such as tablets, gelatin capsules or microgranules.

Although the galenic forms of the invention are particularly appropriate for the administration of active substances which are hydrophilic and/or ionizable in physiological media, they are also suitable for the administration of lipophilic substances.

It may also be noted that the pharmaceutical dosage forms of the invention ensure excellent reproducibility of the results, while allowing increased control of the rate of release during the phase of prolonged release of the active ingredient. By using the pharmaceutical dosage forms of the invention, it becomes possible to optimize the availability of the active ingredients in the body taking into account both the tolerance of the subject to the active ingredient and the pharmacokinetic and metabolic profiles of the active ingredient.

The tablets of the invention are moreover advantageous from the point of view of the formulation of the active ingredients since a judicious choice of the excipients leads to tablets with high concentrations of active ingredients.

The invention provides more precisely orally administrable galenic forms comprising an active ingredient which is hydrophilic and/or ionizable in physiological media, an absorption-promoting agent having an HLB (hydrophilic/lipophilic balance value) greater than 8 and one or more pharmaceutically acceptable excipients.

It should be understood that the galenic forms comprising captopril as active ingredient are excluded from the subject of the invention.

According to the invention, the absorption-promoting agent consists of one or more lipid substances chosen from:
polysorbates; ethers of polyoxyethylene and alkyl; esters of polyoxyethylene and fatty acids; fatty acids; fatty alcohols; bile acids and their salts with pharmaceutically acceptable cations; esters of $C_1$–$C_6$ alkanol with fatty acids; esters of polyol with fatty acids, the said polyol comprising from 2 to 6 hydroxyl functional groups; polyglycolysed glycerides.

These lipid substances are of natural or synthetic origin, or alternatively are obtained by semisynthesis. A good number of them are commercially available or are easily prepared from commercial products.

Although the inventors do not intend to be limited to any mechanism of action, it is thought that by acting on the surface tension of biological fluids, these substances act on membrane contacts at the level of the cells of the gastrointestinal mucous membrane. Whatever the case, it is thought that the absorption-promoting agent creates in situ an environment with modified lipophilicity.

The polysorbates are esters of fatty acids of polyethoxylated sorbitan. Polyethoxylated sorbitan offers polyethoxylated sorbitol and polyethoxylated sorbitol anhydrides. The expression "polysorbate" designates both mono- and poly-esters of fatty acids. Preferably, the polysorbates used according to the invention are mono-, di- or triesters of saturated or unsaturated fatty acids, in which the fatty acids are preferably $C_8$–$C_{22}$, better still $C_{12}$–$C_{18}$. There may be mentioned more particularly monolaurate, monopalmitate, mono- and tristearate, monooleate and monoisostearate.

Preferably, the polysorbates used are the product of the esterification of fatty acids with the copolymer of a molecule of sorbitol or of one of its anhydrides and of 3 to 30 molecules of ethylene oxide.

By way of example, the structural formulae of a monoester and of a triester are given below:

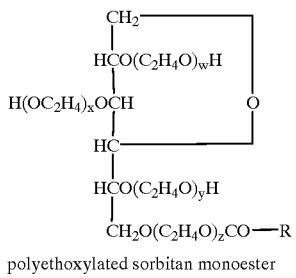

polyethoxylated sorbitan monoester

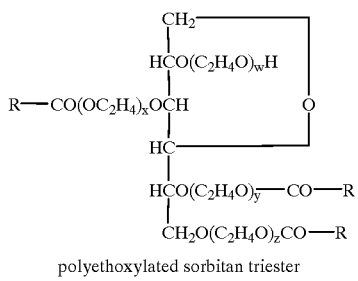

polyethoxylated sorbitan triester where R is the residue of a fatty acid and x, y, z and w are integers whose sum varies between 3 and 30, preferably between 4 and 20.

Generally, polysorbates will be used whose molecular weight varies between 450 and 2000, better still between 500 and 1900.

Such polysorbates are commercially available, especially under the trade name Tween®.

The ethers of polyoxyethylene and alkyl have the general formula:

$$CH_3(CH_2)x(OCH_2CH_2)_yOH$$

in which x is an integer between 8 and 22, preferably between 12 and 18, and y is an integer from 10 to 60. Among these compounds, there may be mentioned monocetyl ether of polyethylene glycol, monolauryl ether of polyethylene glycol, monooleyl ether of polyethylene glycol and monostearyl ether of polyethylene glycol. These compounds are commercially available, especially under the trade name Brij®.

The esters of polyoxyethylene and fatty acids are either fatty acid monoesters of the formula:

$$RCO-(OCH_2CH_2)_n-OH$$

where R represents the residue of a fatty acid and n the degree of polymerization of the polyethoxylated chain, or fatty acid diesters of formula:

$$RCO-(OCH_2CH_2)_n-OCOR$$

where R and n are as defined above,
or mixtures of these monoesters and of these diesters. These compounds are commonly prepared from the corresponding fatty acids and polyethylene glycols.

The polyethylene glycols used as starting material have variable average molecular masses of between 100 and 7000, preferably between 150 and 6000. The starting fatty acids are saturated or unsaturated and generally have from 8 to 22 carbon atoms, better still from 12 to 18 carbon atoms. The esters of polyoxyethylene and fatty acid are especially marketed by the company AKZO-NOBEL The fatty alcohols which can be used according to the invention are saturated or unsaturated, and have preferably from 8 to 22 carbon atoms, better still from 12 to 18 carbon atoms.

The fatty acids are saturated or unsaturated, and have preferably from 8 to 22 carbon atoms, or better still from 12 to 18 carbon atoms.

The bile acids are well known to persons skilled in the art. There may be mentioned glycocholic acid and taurodeoxycholic acid as preferred bile acids. Within the framework of the invention, the promoting agent may comprise a bile acid salt obtained by reacting this acid with a pharmaceutically acceptable base. The salts of alkali and alkaline-earth metals are particularly advantageous, such as sodium glycocholate.

The esters of $C_1$–$C_6$ alkanol with fatty acids can also be used as absorption-promoting agent. Preferably, the fatty acids leading to these esters are as defined above.

The polyol esters are obtained by condensation of one or more fatty acids, as defined above, with a polyol comprising 2 to 6 hydroxyl functional groups. Among these esters, those obtained by esterification of glycols, polyglycerols, sorbitol or its anhydrides are particularly preferred. As glycol, propylene glycol may be mentioned.

The esters of sorbitol or of its anhydrides with one or more fatty acids are fatty acid esters of sorbitan, especially marketed under the trade mark Span®.

The polyglycolysed glycerides are mixtures of glycerides of fatty acids and of esters of polyoxy-ethylene with fatty acids. In these mixtures, the fatty acids are saturated or unsaturated $C_8$–$C_{22}$, for example $C_8$–$C_{12}$ or $C_{16}$–$C_{20}$. The glycerides are mono-, bi- or triglycerides or mixtures thereof in any proportions. Polyglycolysed glycerides are marketed especially by the company Gattefosse under the trade names Labrafil®, Labrasol and Gelucire®.

According to the invention it is essential that the absorption-promoting agent has an HLB greater than 8. Preferably, the HLB is greater than 10; better still it varies between 12 and 16. It should be understood that when the absorption-promoting agent consists of a mixture of several lipid substances, it is the mixture of these substances which should have an HLB greater than 8.

The preferred galenic forms of the invention are those for which the absorption-promoting agent comprises at least one polyglycolised glyceride, especially at least one polyglycolysed glyceride having an HLB of between 12 and 16.

Advantageously, the absorption-promoting agent comprises, in combination with one or more polyglycolysed glycerides, an ester of sorbitan with one or more fatty acids. By way of illustration, the absorption-promoting agent consists of a mixture of one or more polyglycolysed glycerides and a sorbitan ester with a $C_8$–C22 fatty acid, preferably a $C_{16}$–$C_{20}$ fatty acid also having an HLB of between 12 and 16. Among the referred sorbitan esters, there may be mentioned sorbitan monolaurate, sorbitan trilaurate, sorbitan monoisostearate, sorbitan monopalmitate, sorbitan monostearate, sorbitan sesqui-isostearate, sorbitan sesquioleate, sorbitan trioleate and sorbitan tristearate.

Particularly advantageous examples are:

an absorption promoter consisting of Gélucire® 44/14;

an absorption promoter consisting of a mixture of Gelucire® 44/14 and Labrasol®;

an absorption promoter consisting of a mixture of Gelucire® 44/14, Labrasol® and an ester of sorbitan with a $C_{16}$–$C_{20}$ unsaturated fatty acid, such as sorbitan trioleate.

It should be noted that the lipid substances constituting the absorption-promoting agent may also play the role of lubricant, of wetting agent, of thickening agent or of plasticizer.

Thus, glyceryl monostearate and glyceryl palmitostearate have a good lubricating power. Glyceryl monooleate and the fatty acid esters of polyethoxylated sorbitan play the role of wetting agent and the $C_{16}$–$C_{20}$ fatty alcohols and fatty acids (stearic acid, cetyl alcohol), glycerol palmitostearate and more generally some fatty acid glycerides among the monoglycerides, diglycerides and triglycerides are also thickeners. In the same manner, the medium- or short-chain triglycerides act as plasticizers.

Finally, the esters of fatty acid and sorbitan (marketed for example under the name Span®) and the fatty acid esters of polyethoxylated sorbitan (marketed for example under the name Tween®) can be used as additives which may be incorporated into the semisolid matrix for filling gelatin capsules.

The galenic forms of the invention are more particularly intended to improve the absorption of active ingredients which are hydrophilic and/or ionizable in physiological media corresponding to at least one of the following definitions:

(A) active ingredients comprising at least one and generally two functional groups chosen from carboxylic acid, sulphonic acid, phosphoric acid, phosphonic acid, phosphinic acid and phenol functional groups in free form or ionized form with pharmacologically acceptable cations;
(B) the active ingredients comprising at least one and generally two functional groups chosen from the sulphonic acid, phosphoric acid, phosphonic acid and phosphinic acid functional groups in free form or ionized form with pharmacologically acceptable cations;
(C) the active ingredients in the form of calcium salts;
(D) the active ingredients which have the formula (I)

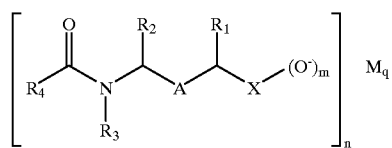

in which
X is chosen from:

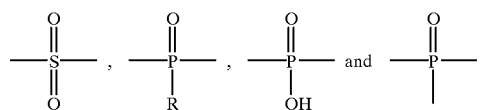

R being a $C_1$–$C_7$ alkyl radical,
$R_1$, $R_2$, $R_3$ are chosen from hydrogen and a $C_1$–$C_7$ alkyl radical,
A represents a group of formula:

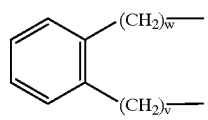

with v and w=0, 1, 2 or a group of formula

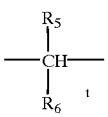

$R_5$, $R_6$ being chosen, independently of each other, from hydrogen, a $C_1$–C7 alkyl radical, an aryl radical having from 6 to 14 carbon atoms and a heteroaryl radical chosen from furyl, thienyl and thiazolyl, it being possible for the aryl and heteroaryl radicals to carry 1 to 3 substituents chosen from a $C_1$–$C_7$ alkyl group, a halogen or a trifluoromethyl group, and t=1–3,
$R_4$ is chosen from hydrogen, a $C_1$–$C_7$ alkyl radical, a $CF_3$ radical, an aryl radical having from 6 to 14 carbon atoms and a heteroaryl radical chosen from furyl, thienyl and thiazolyl, it being possible for the aryl and heteroaryl radicals to carry 1 to 3 substituents chosen from a $C_1$–$C_7$ alkyl group, a halogen or a trifluoromethyl group,
M represents a monovalent metal (Na, K, Li) or a divalent metal (Ca, Mg, Sr, Zn),
m=1 or 2,
p=1–2 and q=1–2, p and q being such that the electrical neutrality of the salt is ensured.
Among these, the following are particularly preferred:
those for which X=

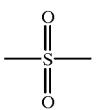

those for which X=

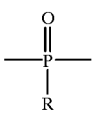

the following compounds:
calcium 3-acetylamino-1-propanesulphonate (or calcium acamprosate)
calcium 3-(2-(methyl)propanoylamino) propanesulphonate
magnesium 3-(2-(methyl)propanoylamino) propanesulphonate
calcium 3-(butanoylamino)propanesulphonate
magnesium 3-(butanoylamino)propanesulphonate
calcium 3-(acetylamino)pentanesulphonate
calcium 3-(pentanoylamino)propanesulphonate
calcium 3-(benzoylamino)propanesulphonate
magnesium 3-(benzoylamino)propanesulphonate
strontium 3-(acetylamino)propanesulphonate
zinc 3-(2-(methyl)propanoylamino)propanesulphonate
strontium 3-(2-(methyl)propanoylamino) propanesulphonate
calcium 3-(3-(methyl)propanoylamino) propanesulphonate
magnesium 3-(3-(methyl)butanoylamino) propanesulphonate
calcium 3-(2,2-(dimethyl)propanoylamino) propanesulphonate magnesium 3-(2,2-(dimethyl)propanoylamino)propanesulphonate
calcium 3-(acetylamino)-2-methylpropanesulphonate
calcium 3-(acetylamino)-3-methylpropanesulphonate
magnesium 3-(acetylamino)-3-methylpropanesulphonate
calcium 3-(acetylamino)-1-methylpropanesulphonate
calcium 3-(acetylamino)-2-phenylpropanesulphonate
calcium 2-(2-acetylaminomethyl)phenylmethanesulphonate
calcium N-(methyl-3-(acetylamino)propanesulphonate
calcium (3-(acetylamino)propyl) ethylphosphinate
calcium 3-(acetylamino)-2-dimethylpropanesulphonate
calcium 3-(trifluoromethylcarbonyl)propanesulphonate;

(E) the active ingredients which are guanidines or guanylguanidines such as metformin or any one of its pharmaceutically acceptable salts and especially metformin hydrochloride;

(F) the active ingredients which are pharmaco-logically acceptable salts of primary, secondary and tertiary amines, such as hydrochlorides, hydrobromides, maleates, acetates, succinates, propionates, fumarates and oxalates;

(G) the active ingredients which, in free form or ionized form with the pharmacologically acceptable cations or anions present in the physiological media, have a solubility greater than 100 g, preferably greater than 250 g per litre;

(H) the active ingredients which, in free form or ionized form with the pharmacologically acceptable cations or anions present in the physiological media, have a partition coefficient D (octanol/water) corresponding to the relationship $\log_{10}D<0$, preferably $\log_{10}D<-0.5$, or better still $\log_{10}D<-20$.

The partition coefficient D is determined in a conventional manner using the "shake flask" technique.

A known quantity of product is introduced into a container containing octanol and water in equal parts (100 ml of water; 100 ml of octanol; the quantity of active ingredient being about $10^{-3}$ M). The mixture is stirred until the product reaches its equilibrium state between the two phases. The phases are then separated. The product may be assayed in both phases by various known methods adapted to the nature of the active ingredient (spectrometry, chromatographic techniques) The partition coefficient D is given by the equation:

$$\text{Log } D = \log (C_{oct}/C_{aq})$$

where
$C_{oct}$: concentration of active ingredient in the octanolic phase;
$C_{aq}$: concentration of active ingredient in the aqueous phase.

As particularly preferred active ingredients, there may be mentioned metformin and acamprosate as well as their pharmacologically acceptable salts.

The pharmacologically acceptable salts are those commonly used in the art. The alkali and alkaline-earth metal salts are examples.

The quantity of active ingredient present in the galenic forms of the invention varies between 0.001 and 95% by weight, preferably between 0.01 and 90%, or better still between 0.1 and 90%.

Depending on the desired effect, persons skilled in the art will incorporate into the galenic compositions of the invention a larger or smaller quantity of absorption-promoting agent. In the general case, the ratio of the active ingredient(s) to the absorption-promoting agent is between 0.001 and 10, for example between 0.01 and 10.

The galenic forms of the invention may be provided in a solid form of the tablet or gelatin capsule type. When the galenic form is a tablet, the ratio of the active ingredient(s) to the absorption-promoting agent is between 1 and 10.

When the galenic form is a gelatin capsule, the ratio of the active ingredient(s) to the absorption-promoting agent is between 0.1 and 2.

The tablets according to the invention may comprise, in combination with the absorption-promoting agent, one or more additional excipients so as to obtain mono- or polyphase tablets. Persons skilled in the art will choose these excipients according to the desired final properties, the application envisaged or so as to overcome a disadvantage linked to the method of manufacturing the tablets.

These excipients exist especially among the following categories: diluents, binders, lubricants, antioxidants, colorants, sweeteners, flavourings and acidulants, wetting agents, hydrophilizing agents such as sorbitol and cyclodextrins, osmotic agents such as mannitol, pH regulators, stabilizing agents such as trehalose and mannitol, adsorbants, chelating and sequestering agents and gastro-resistant film-coating excipients of the type including cellulose acetyl phthalate and polymethacrylates.

By way of example, any one of the following diluents or a combination thereof may be chosen: calcium carbonate, calcium sulphate, sucrose, dextrates, dextrin, dextrose, dicalcium phosphate dihydrate, kaolin, magnesium carbonate, magnesium oxide, maltodextrin, cellulose, microcrystalline cellulose, sorbitol, starches, pregelatinized starch, talc, tricalcium phosphate and lactose.

Among the binders, there may be mentioned: gum arabic, gum tragacanth, guar gum, alginic acid, sodium alginate, sodium carboxymethylcellulose, dextrin, gelatin, hydroxyethylcellulose, hydroxypropylcellulose, liquid glucose, magnesium and aluminium silicate, maltodextrin, povidone, pregelatinized starch, starch and zein.

The lubricants are glidants (such as anhydrous silicate, magnesium trisilicate, magnesium silicate, cellulose, starch, talc or tricalcium phosphate) or alternatively antifriction agents (such as calcium stearate, hydrogenated vegetable oils, paraffin, magnesium stearate, polyethylene glycol, sodium benzoate, sodium lauryl sulphate, fumaric acid, stearic acid or zinc stearate and talc).

As examples of antioxidants, persons skilled in the art can select any of the following compounds: ascorbic acid, ascorbyl palmitate, fumaric acid, propyl gallate, sodium ascorbate and sodium metabisulphite, alpha-tocopherol, malic acid, butylated hydroxytoluene (BHT) and butylated hydroxyanisol (BHA).

Preferred wetting agents are:
sodium docusate and sodium lauryl sulphate which are anionic surfactants;
benzalkonium chloride, benzethonium chloride and cetrimide, which are cationic surfactants;
polyvinyl alcohol and sorbitans, which are non-ionic surfactants.

Among the pH regulators, there may be mentioned acidifiers of the type including citric acid, hydrochloric acid, lactic acid, tartaric acid, as well as alcalinizing agents of the type including monoethanolamine, diethanolamine and triethanolamine, potassium citrate, sodium bicarbonate, sodium citrate dihydrate.

Examples of adsorbants are bentonite, anhydrous colloidal silica, kaolin, magnesium and aluminium silicate, microcrystalline cellulose and cellulose.

As chelating and sequestering agents, there may be used citric acid monohydrate, edetic acid, disodium phosphate, monosodium phosphate, potassium citrate, tartaric acid and sodium citrate dihydrate.

The quantities of these additives are those usually used in the art. In general, the binder may represent from 0.5 to 25% by weight, or better still from 2 to 5% by weight of the tablet.

The lubricants are preferably incorporated into this tablet in an amount of 0.01 to 10% by weight.

As a guide, the quantity of gastro-resistant film-coating excipients varies between 0.5 and 9% by weight of the tablet.

These tablets may be bare, but are preferably film-coated. The film-coating envisaged will make it possible to avoid an unpleasant taste by bringing about masking of the taste. It may participate in modifying the release of the active ingredient and/or of the promoting agent. A gastro-resistant film-coating will make it possible to avoid any release in the stomach; a film-coating which is more hydrophobic and insensitive to pH variations will contribute more towards extending the kinetics of dissolution. Depending on the role attributed to the film-coating, persons skilled in the art will be able to choose the film-forming agent from among the following categories: cellulose derivatives such as hydroxypropylmethylcellulose (HPMC), ethyl cellulose, cellulose acetophthalate, cellulose acetopropionate, cellulose trimelliate, the polymers and copolymers of methacrylic acid and its derivatives. The film-forming agent may be supplemented with:
- plasticizers (such as polyoxyethylene glycols of high molecular weight, esters of polyacids such as citric acid or phthalic acid)
- fillers (such as talc, metal oxides such as titanium oxide)
- colorants chosen from those usable and approved by the pharmaceutical and food industries.

The tablets of the invention are conventionally prepared by a method including the steps of granulation followed by compression. More precisely, the method of manufacture which is the subject of the invention comprises the steps consisting in:
a) preparing a granule of an active substance from a pulverulent mixture of the active substance, to which there would have been added the absorption-promoting agent, preferably in liquid form, agents modifying the kinetics of dissolution, a binding agent and any other excipient which persons skilled in the art will judge to be necessary. The granule formed is called the inner phase.
b) preparing, where appropriate, a pulverulent mixture, termed outer phase, comprising for example cohesion agents, glidants, lubricants.
c) combining, by mixing, the inner and outer phases. It should be noted that all of the constituents of the outer phase may be added and mixed with the excipients of the inner phase during the preparation of the granule ready to be compressed.
d) forming the tablet by compressing the mixture.

Step (a) involves the granulation of powders of amorphous or crystallized particles. This granulation is carried out in a manner known per se and, for example, by a wet granulation method.

The granulation method comprises five essential steps: (i) dry mixing of the various constituents, (ii) wetting, (iii) actual granulation, (iv) drying, and then (v) sizing.

The dry mixing consists of mixing the pulverulent excipients entering into the composition of the granules.

The wetting consists of adding to the pulverulent mixture the various constituents, a wetting liquid which may be water, or an aqueous or organic solution of binder or an alcohol. This is carried out in a mixer-kneader of the planetary, roller, projection or whirling type or a mixer-granulator of the rapid type.

In step (a), the appropriate wetting liquid is water or an alcohol or an aqueous or organic solution of binder, as generally recommended in the art.

According to a particularly preferred embodiment, the absorption-promoting agent is used as wetting liquid for the granulation.

The drying may be carried out in an oven, or in a fluidized air bed dryer, or by microwave.

According to a preferred embodiment of the invention, the sizing is carried out by passing over a screen with a mesh opening of between 0.5 and 1.5 mm, preferably between 0.8 and 1.5 mm.

A preferred mesh opening value is 1.25 mm.

However, the invention does not intend to be limited to the use of a wet granulation method. Thus, persons skilled in the art will also be able to use other existing granulation methods, such as the dry granulation method.

The last step of compression (step d) on an alternating or rotary machine leads to the formation of the tablet.

The galenic forms of the invention may be provided in the form of gelatin capsules or any other substitute material, which may be monolithic, mono- or polyphasic. The content of the gelatin capsule is a matrix of the semisolid type. In this matrix, the active ingredient may be present in dissolved form or alternatively in suspension. The said matrix comprises the absorption-promoting agent described above, the active ingredient and optionally one or more additional excipients chosen from those described below so as to give the preparation the desired properties or so as to overcome the disadvantages linked to the process of preparing the gelatin capsules.

The additional excipients which may be incorporated into the semisolid matrix in combination with the mixture of absorption-promoting agents are of the following categories.
- Wetting agents among which are phospholipids such as the derivatives of phosphatidylcholine or phosphatidylethanolamine better known by the name of natural or purified lecithins.
- Anionic surfactants, such as sodium alkylsulphonates (such as sodium lauryl sulphate or sodium docusate), cationic surfactants such as quaternary ammoniums (such as benzalkonium chloride or benzethonium chloride or cetrimide).
- Thickening agents of the lipid type, among which are vegetable oils (cotton seed, sesame and groundnut oils) and derivatives of these oils (hydrogenated oils such as hydrogenated castor oil, glycerol behenate).
- Thickening agents of the waxy type such as natural carnauba wax or natural beeswax, synthetic waxes such as cetyl ester waxes.
- Thickening agents of the amphiphilic type such as polymers of ethylene oxide (polyoxyethylene glycol of high molecular weight between 4000 and 100000) or propylene and ethylene oxide copolymers (poloxamers).
- Thickeners of the cellulosic type (semisynthetic derivatives of cellulose, hydroxypropylmethylcellulose, hydroxypropylcellulose, hydroxymethylcellulose, of high molecular weight and high viscosity, gum) or any other polysaccharide such as alginic acid.
- Thickening agents of the polymeric type such as acrylic acid polymers (such as carbomers).
- Thickening agents of the mineral type such as colloidal silica, bentonite.

Antioxidants such as ascorbic acid, ascorbyl palmitate, fumaric acid, sodium ascorbate, sodium metabisulphite.

It will be noted that the thickening agents may be added to the mixture of promoting agents in an amount of 0.1 per 1 to 10 per 1. The ratio which exists between the mixture of promoting agents and the mixture of thickening agents determines directly, for the same active ingredient, the kinetics of dissolution of the latter.

The monolithic gelatin capsules of the invention are conventionally prepared by a method including a phase of preparing a semisolid matrix followed by casting into a gelatin capsule.

More precisely, the semisolid matrix is prepared by dispersing, with stirring, the active ingredient in the mixture of the various excipients. The use of subsidiary heating of the container of mixture may be necessary in order to maintain this mixture of excipients in a liquid or semi-pasty state until the phase of casting into a gelatin capsule.

Furthermore, it may be envisaged to cast successively in the same gelatin capsule several semisolid matrices, differing from each other by their active ingredient and/or excipient compositions, thus making possible immediate- and prolonged-type releases which can be adjusted according to pharmacokinetic criteria.

Finally, the method of manufacture may be completed, where appropriate, by sealing the gelatin capsule by bandrolling or any other equivalent system.

It should also be noted that the gelatin capsule form may be replaced by a soft gelatin capsule form or any other substitute material. All the information cited above for the gelatin capsule, both in terms of composition and preparation of the semisolid matrix, remain applicable in this case.

The galenic forms of the invention may be provided in the form of microgranules which may be packaged in a unit dose such as a gelatin capsule, a cachet or a sachet, or even a vial. In this case, the microgranules are obtained by combining the active ingredient and the absorption-promoting agent with one or more excipients chosen from the following categories:

Diluents such as calcium carbonate, calcium sulphate dihydrate, sucrose, lactose, dextrates, dextrin, dextrose, dicalcium phosphate dihydrate, kaolin, magnesium carbonate, magnesium oxide, maltodextrin, microcrystalline cellulose, sorbitol, mannitol, starches, talc, tricalcium phosphate.

Thickening agents of the lipid type, among which are vegetable oils (cotton seed, sesame and groundnut oils) and derivatives of these oils (hydrogenated oils such as hydrogenated castor oil, glycerol behenate).

Thickening agents of the waxy type such as natural carnauba wax or natural beeswax, synthetic waxes such as cetyl ester waxes.

Thickening agents of the amphiphilic type such as polymers of ethylene oxide (polyoxyethylene glycol of high molecular weight between 4000 and 100000) or propylene and ethylene oxide copolymers (poloxamers).

Thickeners of the cellulosic type (semisynthetic derivatives of cellulose, hydroxypropylmethylcellulose, hydroxypropylcellulose, hydroxymethylcellulose, of high molecular weight and high viscosity, gum) or any other polysaccharide such as alginic acid.

Thickening agents of the polymeric type such as acrylic acid polymers (such as carbomers).

Thickening agents of the mineral type such as colloidal silica, bentonite.

Antioxidants such as ascorbic acid, ascorbyl palmitate, fumaric acid, sodium ascorbate, sodium metabisulphite.

Effervescent mixtures are some of the agents capable of being incorporated into the microgranules. These mixtures are composed, on the one hand, of alkali or alkaline-earth metal carbonates or sodium glycin carbonate, and, on the other hand, of organic acids such as citric acid or tartaric acid. Polymers of the cellulosic type (hydroxypropylmethylcellulose, hydroxypropylcellulose, hydroxymethylcellulose, of high molecular weight and high viscosity) or any other polysaccharide such as alginic acid or of polyacrylic type (carbomers) may also be used in combination. This combination makes it possible to obtain microgranules having good floatability in biological media.

These microgranules may be bare, but are preferably film-coated. The film-coating envisaged will make it possible to avoid an unpleasant taste by bringing about masking of the taste. It may participate in modifying the release of the active ingredient and/or of the promoting agent. A gastro-resistant film-coating will make it possible to avoid any release in the stomach; a film-coating which is more hydrophobic and insensitive to pH variations will contribute more towards extending the kinetics of dissolution. Depending on the role attributed to the film-coating, persons skilled in the art will be able to choose the film-forming agent from among the following categories: cellulose derivatives such as hydroxypropylmethylcellulose, ethyl cellulose, cellulose acetophthalate, cellulose acetopropionate, cellulose trimelliate, the polymers and copolymers of methacrylic acid and its derivatives. The film-forming agent will be supplemented with:

plasticizers (such as polyoxyethylene glycols of high molecular weight, esters of polyacids such as citric acid or phthalic acid)

fillers (such as talc, metal oxides such as titanium oxide).

colorants chosen from those usable and approved by the pharmaceutical and food industries.

The rate of film-coating may vary from 2 to 25% of the weight of the bare microgranules, preferably from 4 to 20% and more preferably from 5 to 20%.

Furthermore, it may be envisaged to fill the same gelatin capsule with different types of microgranules, differing from each other by their active ingredient and/or absorption-promoting agent and/or excipient compositions, or to even combine bare and film-coated microgranules, making it possible to adjust the kinetics of release of the active ingredient.

The microgranules are conventionally prepared by a method including incorporation of the mixture of absorption-promoting agents with the pulverulent mixture of the other excipients and of the active ingredient(s) into a high-speed mixer, followed by nucleation, swelling and spheronization.

As regards the film-coating phase, it is conventionally carried out by spraying a suspension of film-forming agent and additives over a mass of moving microgranules in a turbine or more advantageously in a fluidized air bed apparatus.

The microgranules or a mixture thereof are placed in gelatin capsules in conventional manner using a filling device. For the latter operation, the incorporation of additives such as glidants, lubricants or even diluents may prove necessary. Persons skilled in the art will be able to choose either of these compounds from among the excipients cited in the corresponding paragraphs above.

It should be noted that the microgranules may have a size of between 0.1 and 3 mm, preferably between 0.2 and 2 mm and more preferably between 0.3 and 1.5 mm.

Furthermore, it is possible to envisage the production of tablets from the preceding microgranules. In this case, the cohesion of the tablets can be ensured by virtue of the addition of other microgranules or of a granule prepared in a conventional manner with the excipients conventionally used for this purpose.

In order to easily control the kinetics of release of the active ingredient, it is desirable to incorporate one or more of the following constituents into the galenic forms of the invention:

glycerol palmitostearate;

a hydrogenated castor oil;

glycerol behenate; or stearic acid.

The addition of polymeric derivatives may also be envisaged for this purpose.

As appropriate polymeric substance, there may be mentioned semisynthetic celluloses of high molecular weight, carbomers such as polyacrylic acids, polymers and copolymers of methacrylic acid and its derivatives.

The examples provided in the remainder of this text illustrate the invention in greater detail. This will be done with reference to FIGS. 1 to 9.

For the sake of simplicity, all the formulations described below have 500-mg doses of active ingredient.

In the following examples, the active ingredient is calcium acamprosate (or calcium acetylhomotaurinate) designated ACA in the text which follows.

Precirol® and Precirol ATO5® are glycerol palmitostearate marketed by the company Gattefosse.

Compritol® is glycerol behenate marketed by the company Gattefosse.

Methocel K15M® is hydroxypropylcellulose marketed by the company Colorcon.

Eudragit RS 30D® is a copolymer of acrylic acid ester and methacrylic acid esters, containing a low content of ammonium groups available from the company Rohm.

EXAMPLE 1

Gelatin capsule containing a semisolid matrix providing immediate release of the active ingredient.

The constituents for the preparation of the immediate-release semisolid matrix were used in the following proportions (by weight):

| | |
|---|---|
| ACA | 54% |
| Gélucire 44/14 ® | 45% |
| Soya bean lecithin | 1% |

The excipients are melted at a temperature greater than their melting point, their mixture is homogenized and then the active ingredient is incorporated. The mixture is cast into gelatin capsules of size 00 in a sufficient quantity.

EXAMPLE 2

Dissolution profile for the gelatin capsules manufactured according to the procedure of Example 1.

The dissolution profiles for the gelatin capsules manufactured in the preceding example were determined after assaying by high-performance liquid chromatography.

The gelatin capsules to be tested are introduced into reactors which were each previously filled with one litre of distilled water, at 37° C., and provided with a temperature regulating system and an efficient stirring system.

During the whole experiment, the reactor is kept stirred at 37° C.

At regular time intervals t, samples of the medium contained in the reactor are collected, filtered on a membrane of porosity 0.45 µm (Millex HA, in cellulose acetate) and analysed by high-performance liquid chromatography (HPLC) with detection by UV spectrophotometry.

Conditions for analysis by HPLC.

Column having a length of 10 cm and an internal diameter of 4.6 mm, filled with 5-µm particles of octadecylsilylated silica.

Mobile phase: tetrabutylammonium perchlorate solution at 341.9 mg in 1000 ml of a water/acetonitrile: 95/5 mixture.

The detection is carried out by UV spectrophotometry at 200 nm.

The quantity q of active ingredient present in the sample is determined by comparison with the area of the peak obtained under the same conditions with a reference solution of known concentration. A simple calculation makes it possible to find the total quantity of active ingredient released into the reactor at the instant t.

The dissolution profile of the gelatin capsule is obtained by plotting on a curve the calculated quantities of active ingredient (expressed in percentage of the nominal dose) as a function of time. (See FIG. 1).

EXAMPLE 3

Gelatin capsules containing a semisolid matrix providing immediate release of the active ingredient.

The table below gives the composition by weight of each of the gelatin capsules.

| Composition | Gelatin capsule 3.1 | Gelatin capsule 3.2 | Gelatin capsule 3.3 | Gelatin capsule 3.4 | Gelatin capsule 3.5 | Gelatin capsule 3.6 |
|---|---|---|---|---|---|---|
| ACA | 47% | 47% | 51% | 51% | 51% | 50% |
| Gélucire 44/14 ® | 39% | 39% | 30% | 28% | 25% | 30% |
| Labrasol ® | 13% | — | 18% | 20% | 23% | 18% |
| PEG 400 | — | 13% | — | — | — | — |
| Sorbitan trioleate | — | — | — | — | — | 2% |
| Soya bean lecithin | 1% | 1% | 1% | 1% | 1% | — |
| HLB | 14 | 14 | 14 | 14 | 14 | 13.5 |

The procedure is the same as that of Example 1.

EXAMPLE 4

Gelatin capsules containing a semisolid matrix providing prolonged release of the active ingredient. The table below gives the composition by weight of each of the gelatin capsules.

| Composition | Gelatin capsule 4.1 | Gelatin capsule 4.2 |
|---|---|---|
| ACA | 54% | 54% |
| Gélucire 44/14 ® | 32% | 22.5% |
| Précirol ® | 13% | 22.5% |
| Soya bean lecithin | 1% | 1% |

The procedure is the same as that of Example 1.

EXAMPLE 5

Gelatin capsules containing a semisolid matrix providing prolonged release of the active ingredient.

The table below gives the composition by weight of each of the gelatin capsules.

| Composition | Gelatin capsule 5.1 | Gelatin capsule 5.2 | Gelatin capsule 5.3 | Gelatin capsule 5.4 | Gelatin capsule 5.5 |
|---|---|---|---|---|---|
| ACA | 54% | 54% | 54% | 54% | 54% |
| Gélucire 44/14 ® | 38% | 36% | 34% | 32% | 29% |
| Précirol ® | 7% | 9% | 11% | 13% | 16% |
| Soya bean lecithin | 1% | 1% | 1% | 1% | 1% |

The procedure is the same as that of Example 1. The dissolution profiles obtained for these gelatin capsules by applying the analytical method of Example 2 are given in FIG. 2.

EXAMPLE 6

Gelatin capsules containing a semisolid matrix providing prolonged immediate release of the active ingredient.

Gelatin capsules were filled both with a matrix obtained according to Example 1 and a matrix obtained according to Example 4, gelatin capsule 4.5. The weight ratio of the matrix of Example 1 to the matrix of Example 4 is 1:2.

EXAMPLE 7

Gelatin capsules filled with microgranules for immediate release of the active ingredient.

The constituents for the preparation of the immediate-release microgranules were used in the following proportions by weight:

| Composition | Gelatin capsule 7.1 | Gelatin capsule 7.2 | Gelatin capsule 7.3 |
|---|---|---|---|
| ACA | 50% | 75% | 85% |
| Gélucire 44/14 ® | 16% | 14% | 15% |
| Lactose | 34% | 11% | — |

The pulverulent active ingredient and the excipient are introduced into a mixer of the rapid type. After the phases of melting of the excipient and then nucleation followed by swelling of the granules, the latter are spheronized.

Figure 3:
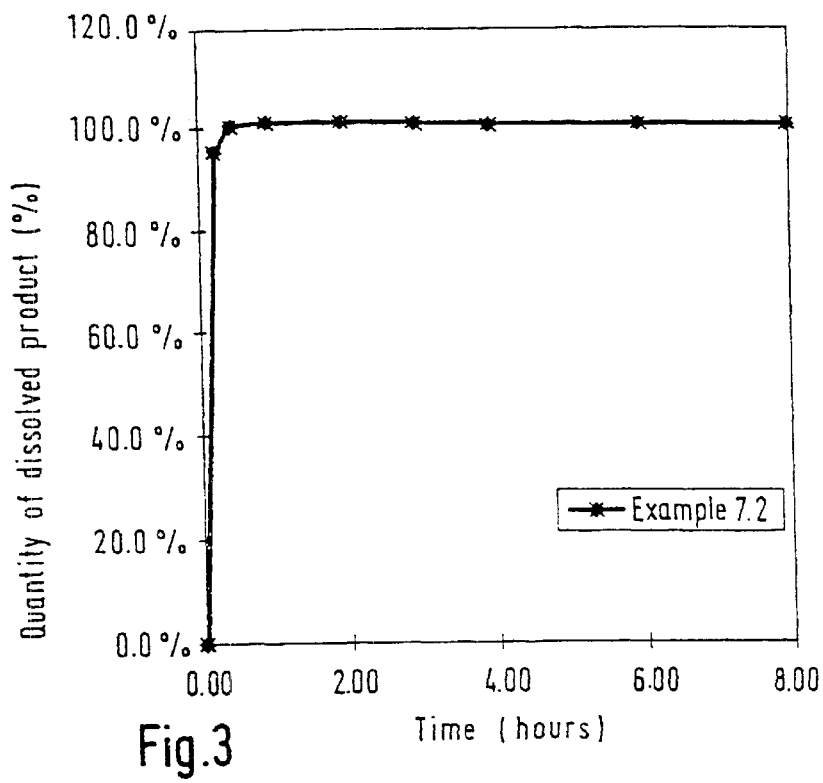

The dissolution profile obtained for the gelatin capsule 7.2 by applying the analytical method of Example 2 is given in FIG. 3.

EXAMPLE 8

Gelatin capsules filled with microgranules for immediate release of the active ingredient.

The constituents for the preparation of the immediaterelease microgranules were used in the following proportions (by weight):

| ACA | 85% |
|---|---|
| Gélucire 50/13 ® | 15% |

The method of manufacture which served for the manufacture of the microgranules of Example 7 was also used in this example.

EXAMPLE 9

Gelatin capsule filled with microgranules for the prolonged release of the active ingredient.

The constituents for the preparation of the immediate-release microgranules were used in the following proportions (by weight):

| ACA | 25% |
|---|---|
| Précirol ® | 18% |
| Lactose | 57% |

The method of manufacture which served for the manufacture of the microgranules of Example 7 was also used in this example.

Figure 4:
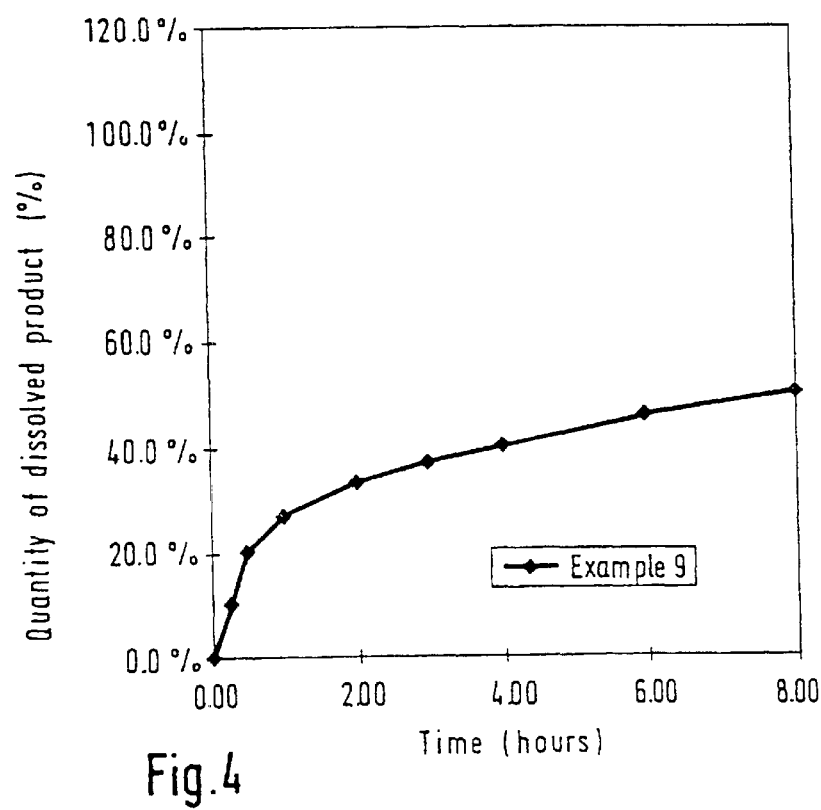

The dissolution profile obtained for this gelatin capsule by applying the analytical method of Example 2 is given in FIG. 4.

EXAMPLE 10

Gelatin capsules filled with microgranules for the prolonged release of the active ingredient.

The constituents for the preparation of the prolonged-release microgranules were used in the following proportions by weight:

| Composition | Gelatin capsule 10.1 | Gelatin capsule 10.2 | Gelatin capsule 10.3 |
|---|---|---|---|
| ACA | 75% | 75% | 75% |
| Gélucire 50/13 ® | 7% | 3.5% | 1% |
| Compritol ® | 7% | 10.5% | 13% |
| Lactose | 11% | 11% | 11% |

The method of manufacture which served for the manufacture of the microgranules of Example 7 was also used in this example.

The dissolution profiles obtained for these gelatin capsules by applying the analytical method of Example 2 are given in FIG. 5.

EXAMPLE 11

Gelatin capsules filled with microgranules with high floatability.

The constituents for the preparation of these microgranules were used in the following proportions by weight:

| | |
|---|---|
| ACA | 50% |
| Gélucire 44/14 ® | 9% |
| Précirol ATO 5 ® | 9% |
| Methocel K15 M ® | 15% |
| Citric ac. | 4% |
| Na bicarbonate | 8% |
| Lactose | 5% |

The method of manufacture which served for the manufacture of the microgranules of Example 7 was also used in this example.

EXAMPLE 12

Gelatin capsules filled with microgranules for the prolonged release of the active ingredient.

The constituents for the preparation of the prolonged-release microgranules were used in the following proportions:

| | |
|---|---|
| ACA | 74% |
| Gélucire 44/14 ® | 13% |
| Eudragit RS 30D ® | 9% |
| Talc | 3% |
| Triethyl citrate | 1% |

The manufacture can be separated into two stages:

The microgranules obtained in Example 7.3 were film-coated using the following suspension of film-forming agent,

| | |
|---|---|
| Suspension of Eudragit RS 30D ® | 250 g |
| Talc | 22.50 g |
| Triethyl citrate | 11.25 g |
| Distilled water | 260 g |

The film-coating operation is carried out in a fluidized air bed apparatus.

EXAMPLE 13

Gelatin capsules filled with microgranules for the prolonged release of the active ingredient.

The constituents for the preparation of the prolonged-release microgranules were used in the following proportions by weight:

| Composition | Gelatin capsule 13.1 | Gelatin capsule 13.2 | Gelatin capsule 13.3 |
|---|---|---|---|
| ACA | 80% | 74% | 66% |
| Gélucire 44/14 ® | 14% | 13% | 12% |
| Ethyl cellulose | 6% | 13% | 22% |

The manufacture can be separated into two stages:

The microgranules obtained in Example 7.3 were film-coated using the following suspension of film-forming agent,

| | |
|---|---|
| Surelease ® (aqueous suspension of ethyl cellulose) | 300 g |
| Distilled water | 200 g |

The film-coating operation is carried out in a fluidized air bed apparatus.

The dissolution profiles obtained for these gelatin capsules by applying the analytical method of Example 2 are given in FIG. 6.

EXAMPLE 14

Gelatin capsules filled with two types of microgranules for the immediate and prolonged release of the active ingredient.

The constituents for the preparation of the immediate- and prolonged-release microgranules were used in the following proportions:

| | |
|---|---|
| ACA | 78% |
| Gélucire 44/14 ® | 14% |
| Ethyl cellulose | 8% |

The gelatin capsules were prepared by filling with a mixture of bare microgranules (obtained in Example 7.3) and of the film-coated microgranules (obtained in Example 13.2). The weight ratio of the microgranules of Example 7.3 to the microgranules of Example 13.2 is 40:60.

Figure 7:
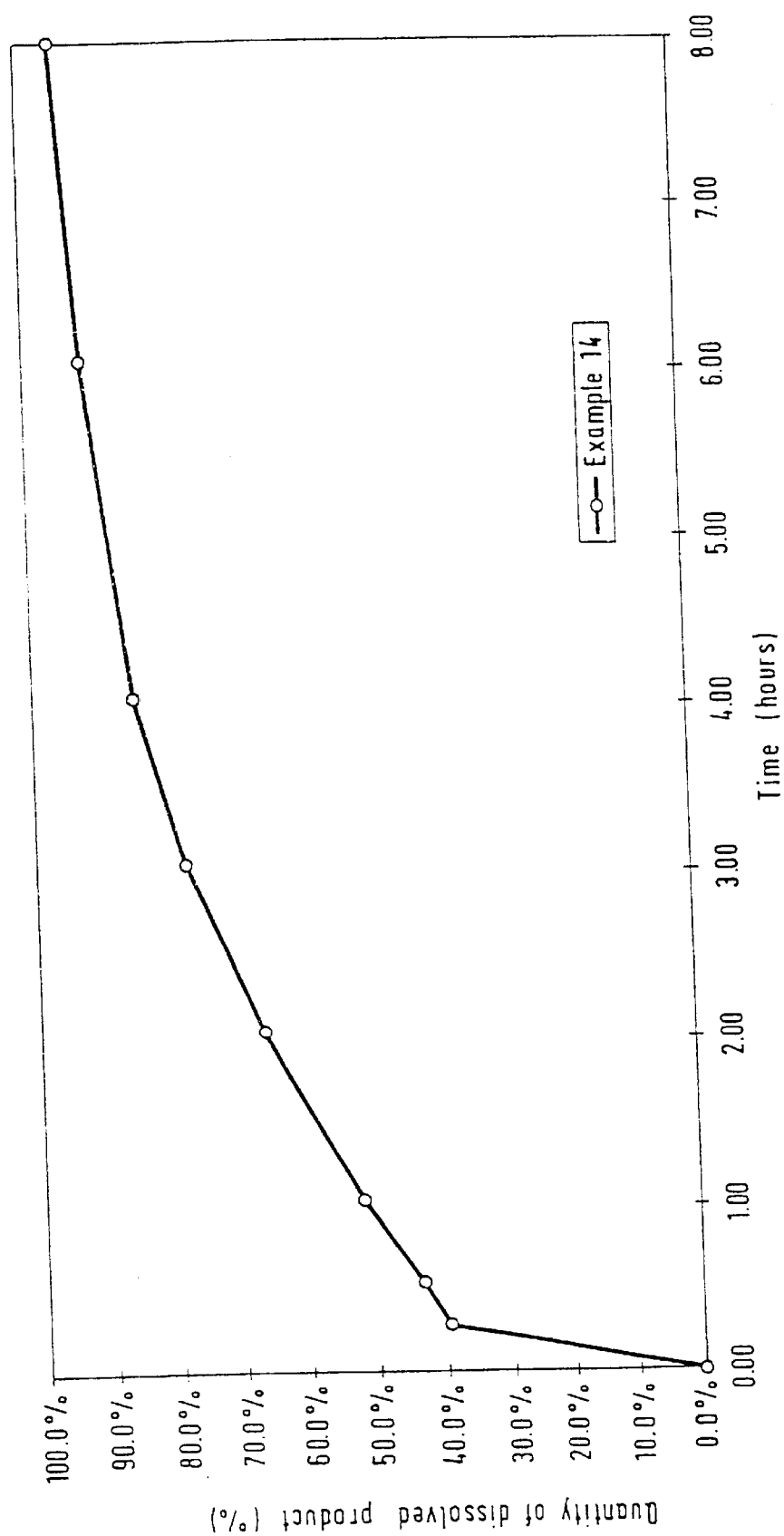

The dissolution profile obtained for this gelatin capsule by applying the analytical method of Example 2 is given in FIG. 7.

EXAMPLE 15

Tablets for the immediate and prolonged release of the active ingredient.

The constituents for the preparation of the tablets for immediate and prolonged release were used in the following proportions by weight:

| Composition | Tablet 15.1 | Tablet 15.2 | Tablet 15.3 | Tablet 15.4 |
|---|---|---|---|---|
| ACA | 50% | 50% | 50% | 50% |
| Gélucire 44/14 ® | 10% | 10% | 10% | 10% |
| Compritol ® | 20% | 20% | 10% | 10% |
| Microcrystalline cellulose | 9% | 14% | 19% | 24% |
| Povidone | 10% | 5% | 10% | 5% |
| Mg stearate | 1% | 1% | 1% | 1% |

The active ingredient is introduced into a rapid mixer-granulator, the molten Gélucire is added with stirring.

Compritol®, povidone and microcrystalline cellulose are then added to this pulverulent mixture which is subjected to stirring. The wetting liquid, purified water, is then added until well-formed granules and agglomerates are obtained.

The whole is then dried (oven or fluidized air bed) and sized on a screen with a mesh opening of 1.25 mm.

The dry granule is introduced into a rapid mixed-granulator, and then magnesium stearate is added.

The lubricated granule is compressed on a rotary machine equipped, for example, with oblong dies.

Figure 8:
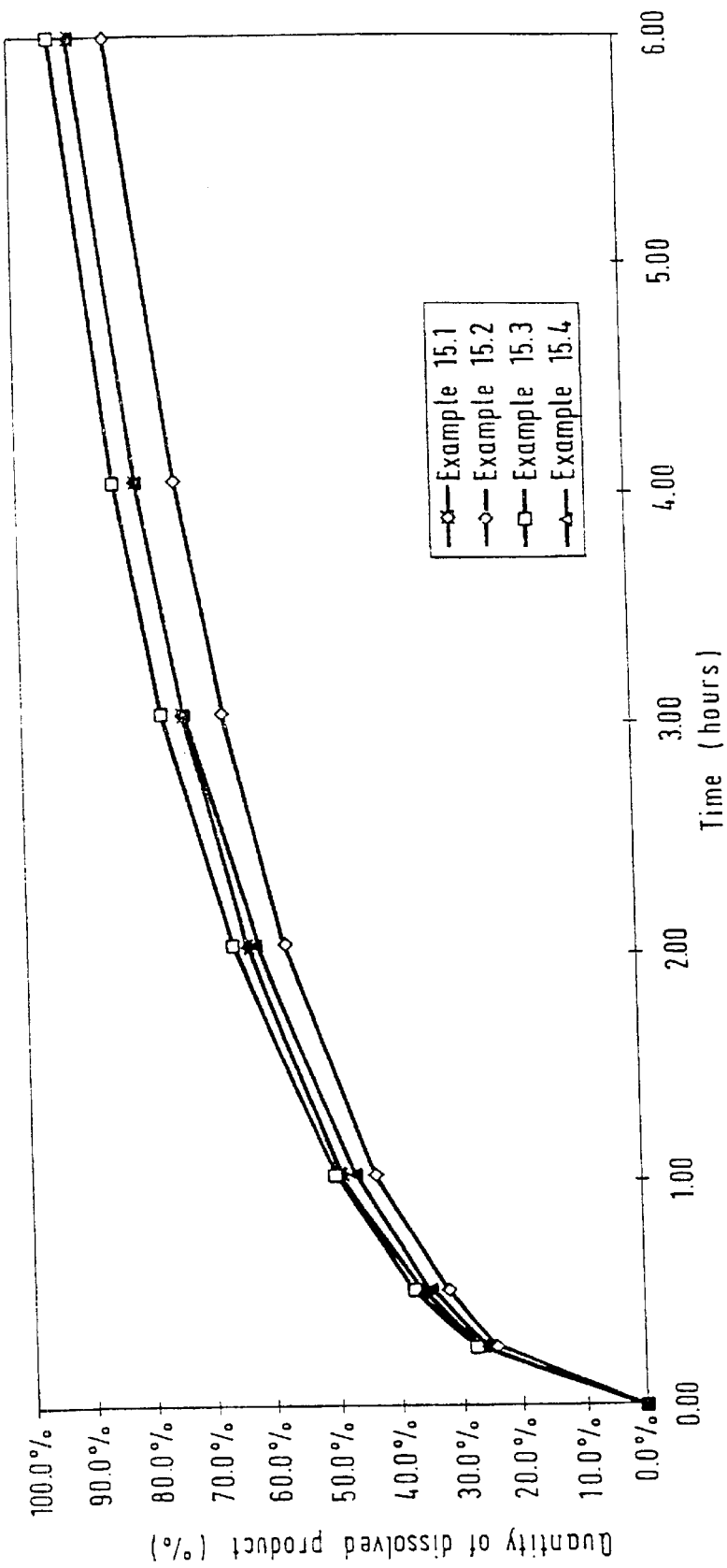

The dissolution profiles obtained for these tablets by applying the analytical method of Example 2 are given in FIG. 8.

EXAMPLE 16

Tablets for the immediate and prolonged release of the active ingredient.

The constituents for the preparation of these tablets were used in the following proportions by weight:

| Composition | |
|---|---|
| Bare core | |
| ACA | 50% |
| Gélucire 44/14 ® | 10% |
| Compritol ® | 10% |
| Microcrystalline cellulose | 19% |
| Povidone | 10% |
| Mg stearate | 1% |
| Film-coating | |
| HPMC | 64% |
| PEG 4000 | 15% |
| Talc | 21% |

The method of manufacture comprises two stages. The preparation of the bare cores is carried out as in Example 15; it is followed by film-coating in a turbine by spraying a suspension.

EXAMPLE 17

Tablets for the immediate and prolonged release of the active ingredient.

The constituents for the preparation of these tablets were used in the following proportions by weight:

| Composition | |
|---|---|
| Bare core | |
| ACA | 47.5% |
| Gélucire 44/14 ® | 9.5% |
| Compritol ® | 9.5% |
| Microcrystalline cellulose | 18% |
| Povidone | 9.5% |
| Mg stearate | 1% |
| Talc | 5% |
| Film-coating | |
| HPMC | 64% |
| PEG 4000 | 15% |
| Talc | 21% |

The method of manufacture comprises two stages. The preparation of the bare cores is carried out as in Example 15; it is followed by film-coating in a turbine by spraying a suspension.

Figure 9:
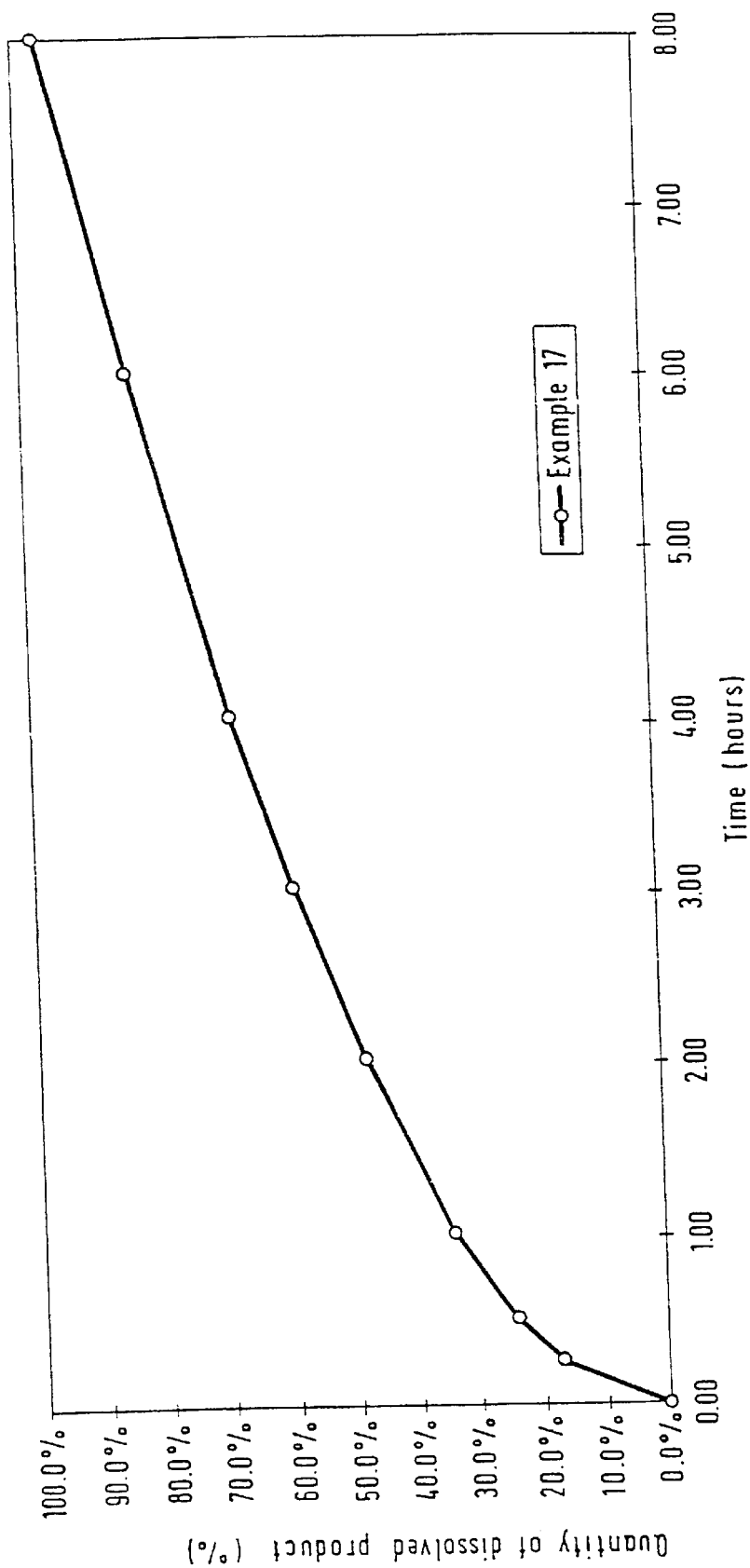

The dissolution profile obtained for this tablet by applying the analytical method of Example 2 is given in FIG. 9.

EXAMPLE 18

Actions of various promoting agents or mixtures of promoting agents on the permeability of calcium acetylhomotaurinate, in the Caco-2 cellular model.

A solution of carbon 14-labelled acamprosate, of known concentration, is placed in the apical compartment of a Grass Sweetana-type diffusion chamber which comprises a second so-called basolateral compartment separated from the first by an insert supporting a monocellular confluent culture of human colon adenocarcinoma endothelium epithelial cells, Caco-2 line.

Samples are collected at regular intervals from the second basolateral compartment. The acamprosate concentration is determined by scintigraphy. A simple calculation makes it possible to obtain the apparent permeability coefficient (Papp). The acamprosate solution is supplemented with various promoting agents or mixtures of promoting agents, under varying conditions. The influence of these agents on the apparent permeability coefficient (Papp) was measured. The experimental results are grouped together in the following table where the apparent permeability coefficient values (Papp) are expressed in cm/s.

Action of the absorption-promoting agents:
Appearance Permeability Coefficient

| | | Category of Absorption-Promoting Agent | | | | | | | | | | | | |
|---|---|---|---|---|---|---|---|---|---|---|---|---|---|---|
| | | Gélucire | | | | PEG | | Fatty Ac | | Labrafil | | glyco chol- | | Na Polysorbate |
| Type | None | 44/14 | | | 37/02 | 4000 | | Capric Capryl | | 1944 cs | | ate | | 80 |
| Conc. (% m/v) | | 0.10 | 1.0 | 5.0 | 1  5 | 1 | 5 | 0.25 | 0.25 | 1.0 | 5.0 | 0.2 | 0.05 | 0.50  5.0 |
| Papp ($10^{-7}$ cm/s) | | | | | | | | | | | | | | |
| Mean (n = 6) | 24.0 | 152.0 | 618.6 | 1030 | 47.0  55.8 | 58.5 | 12.3 | 63.6 | 94.3 | 61.1 | 206.0 | 114 | 27.6 | 186.0  409.0 |
| Standard deviation | 1.1 | 12.9 | 12.1 | 216.0 | 9.2  9.4 | 30.7 | 1.2 | 11.0 | 17.6 | 28.4 | 33.1 | 11.9 | 1.8 | 56.5  106.0 |

EXAMPLE 19

Increase in the bioavailability of calcium aceylhomotaurinate in Beagle dogs by means of an immediate-release oral form.

The relative bioavailability of calcium-acetylhomotaurinate was determined after administration of various immediate-release oral formulations, and in comparison with a reference formulation: gastroresistant tablets at 333 mg.

Protocol:

The study was carried out on 5 dogs of Beagle breed. On the day of the administration, the dogs, starved from the day before, successively received at an interval of one week, by the oral route, one of the following galenic forms:

| Formulation | Dose of acamprosate per unit (mg) | Number of units administered |
|---|---|---|
| Reference formulation (1) | 333 | 2 |
| Reference tablet supplemented with 100 mg of sodium glycocholate (2) | 333 | 2 |
| Gelatin capsule with semisolid matrix of Example 1 | 500 | 1 |
| Floating tablet at 500 mg (3) | 500 | 1 |
| Immediate-release gelatin capsule with micro-granules of Example 7.1 | 500 | 1 |

(1) Unit composition of the reference tablet 1

Cores

| | |
|---|---|
| Acamprosate | 333 mg |
| Crospovidone | 10 mg |
| Microcrystalline cellulose | 100 mg |
| Magnesium silicate | 30 mg |
| Starch glycolate | 10 mg |
| Colloidal silica | 3 mg |
| Magnesium stearate | 7 mg |

Film-coating

| | |
|---|---|
| Eudragit L 30D | 27.9 mg |
| Talc | 6.5 mg |
| Propylene glycol | 4.2 mg |

(2) Unit composition of the tablets supplemented with sodium glycocholate 2

Cores

| | |
|---|---|
| Acamprosate | 333 mg |
| Sodium glycocholate | 100 mg |
| Crospovidone | 10 mg |
| Microcrystalline cellulose | 100 mg |
| Magnesium silicate | 30 mg |
| Starch glycolate | 10 mg |
| Colloidal silica | 3 mg |
| Magnesium stearate | 7 mg |

Film-coating

| | |
|---|---|
| Eudragit L 30D | 27.9 mg |
| Talc | 6.5 mg |
| Propylene glycol | 4.2 mg |

(3) Unit composition of floating tablets at 500 mg.

| | |
|---|---|
| Acamprosate | 500 mg |
| Hydroxypropylmethylcellulose | 550 mg |
| Povidone | 80 mg |
| Microcrystalline cellulose | 80 mg |
| Sodium bicarbonate | 250 mg |
| Talc | 7 mg |
| Magnesium stearate | 6 mg |

Blood samples were collected just before the administration, and then 0.5; 1; 2; 3; 4; 5; 6; 8 and 24 hours after the administration. Using these samples, plasma acamprosate was assayed by gas chromatography/mass spectrometry (GC/MS). The following pharmacokinetic parameters were then determined for each administered form:

Maximum value of plasma acamprosate (Cmax), area under the curve of the plasma concentrations (AUC), relative bioavailability of the oral form tested (F), established according to the formula:

Dose(reference)×AUC (tested)/F=dose(tested)×AUC(reference)

The mean pharmacokinetic parameters observed for each of the forms tested are presented in the table below:

TABLE 1

Mean pharmacokinetic parameters for acamprosate observed in Beagle dogs after single oral administration of various immediate-release galenic forms versus the reference form.

| Formulation | C max (ng/ml) | F (ref. 666 mg) % |
|---|---|---|
| Reference formulation 2 tablets at 333 mg | 17,593 | 100 |
| 2 tablets at 333 mg supplemented with 100 mg of sodium glycocholate | 7921 | 68 |
| Gelatin capsule with semisolid matrix of Example 1 | 16,935 | 138 |
| Floating tablet at 500 mg | 15,072 | 138 |
| Immediate-release gelatin capsule with micro-granules of Example 7.1 | 19,543 | 146 |

Conclusion:

The gelatin capsule form containing semisolid matrix of Example 1 and the immediate-release gelatin capsule form filled with microgranules of Example 7.1 allow an increase of about 40% in the relative bioavailability of calcium acetylhomotaurinate.

EXAMPLE 20

Increase in the bioavailability of calcuim acetylhomotaurinate in Beagle dogs by means of a prolonged-release oral form.

The relative bioavailability of calcium acetylhomotaurinate was determined after administration of various prolonged-release oral formulations, and in comparison with two reference formulations: gastroresistant tablets at 500 mg and a formulation in the form of immediate-release gelatin capsules (Example 1). Furthermore, comparison of the plasma levels at 6 and 24 hours was carried out for all the forms tested.

Protocol: The study was carried out on 6 dogs of Beagle breed. On the day of the administration, the dogs, starved from the day before, successively received at an interval of one week, by the oral route, one of the following galenic forms:

| Formulation | Dose per unit (mg) | Number of units administered |
|---|---|---|
| Reference 1: gastro resistant tablet (1) | 500 | 2 |
| Reference 2: immediate-release gelatin capsule with semisolid matrix Example 1 | 500 | 1 |
| Prolonged-release matrix tablet Example 15.3 | 500 | 1 |
| Prolonged-release gelatin capsule with semisolid matrix Example 4.1 | 500 | 1 |
| Prolonged-release gelatin capsule with semisolid matrix Example 4.2 | 500 | 1 |
| Gelatin capsule with microgranules Example 14 | 500 | 1 |

| (1) Unit composition of the gastroresistant 500-mg tablets | |
|---|---|
| Cores | |
| Acamprosate | 500 mg |
| Crospovidone | 15 mg |
| Microcrystalline cellulose | 150 mg |
| Magnesium silicate | 45 mg |
| Starch glycolate | 15 mg |
| Colloidal silica | 4.5 mg |
| Magnesium stearate | 10.5 mg |
| Film-coating | |
| Eudragit L 30D | 31.1 mg |
| Talc | 7.2 mg |
| Propylene glycol | 4.5 mg |

Blood samples were collected just before the administration, and then 0.5; 1; 2; 3; 4; 5; 6; 8 and 24 hours after the administration. Using these samples, plasma acamprosate was assayed according to an LC/MS method. The following pharmacokinetic parameters were then determined for each administered form:

Maximum value of plasma acamprosate (Cmax), the plasma levels at 6 hours ($C(_6h)$) and at 24 hours ($C(_{24}h)$), area under the curve of the plasma concentrations (AUC), relative bioavailability of the oral form tested (F), established according to the formula:

$$F = \frac{\text{Dose (reference)} \times AUC(\text{tested})}{\text{dose (tested)} \times AUC(\text{reference})}$$

Result:
The mean pharmacokinetic parameters observed for each of the forms tested are presented in the table below:

TABLE 2

Mean pharmacokinetic parameters for acamprosate observed in Beagle dogs after single oral administration of various modified-release galenic forms versus an immediate form.

| Mean | Cmax (ng/ml) | Frel. (%) | C (6 h) | C (24 h) |
|---|---|---|---|---|
| Reference 2: immediate-release gelatin capsule with semisolid matrix Example 1 | 20,868 | 100 | 3433 | 69 |
| Gelatin capsule with microgranules Example 14 | 12,448 | 67 | 2448 | 32 |
| Prolonged-release matrix tablet Example 15.3 | 20,753 | 99 | 3916 | 261 |
| Prolonged-release gelatin capsule with semisolid matrix Example 4.1 | 19,175 | 111 | 4471 | 82 |
| Prolonged-release gelatin capsule with semisolid matrix Example 4.2 | 9363 | 64 | 3470 | 99 |

Conclusions:
The matrix tablet form (Example 15.3) and the semisolid gelatin capsule form (Example 4.1) make it possible to maintain or even increase the relative bioavailability of acamprosate, and furthermore the levels observed respectively at 6 h and 24 h are greater than those observed for the reference gelatin capsule: Example 1.

EXAMPLE 21

Evaluation of the relative bioavailability, of the pharmacokinetic parameters and of the tolerance of two forms of acamprosate versus the reference form (2×500 mg) after a single administration by the oral route. Open and crossover studies in 18 healthy male volunteers.

The relative bioavailability of two galenic forms containing 500 mg of calcium acetylhomotaurinate was evaluated in men in comparison with a reference formulation, also containing 500 mg but of which 2 unit doses were administered.

Summary of the study:
The following products were randomly administered to 18 healthy subjects, of male sex, of Caucasian origin, aged from 18 to 45 years:
- a reference product R: 2 immediate-release gastroresistant tablets containing 500 mg doses (on an empty stomach).
- a so-called "floating" tablet F containing a 500 mg dose (not on an empty stomach).
- a gelatin capsule G with semisolid matrix containing a 500 mg dose: Example 1 (on an empty stomach).

| Unit composition of the 500 mg gastroresistant tablets: R | |
|---|---|
| Cores | |
| Acamprosate | 500 mg |
| Crospovidone | 15 mg |
| Microcrystalline cellulose | 150 mg |
| Magnesium silicate | 450 mg |
| Starch glycolate | 15 mg |
| Colloidal silica | 4.5 mg |
| Magnesium stearate | 10.5 mg |
| Film-coating | |
| Eudragit L 30D | 31.1 mg |
| Talc | 7.2 mg |
| Propylene glycol | 4.5 mg |

-continued

| Unit composition of the floating tablets at 500 mg: F | |
|---|---|
| Acamprosate | 500 mg |
| Hydroxypropylmethylcellulose | 550 mg |
| Povidone | 80 mg |
| Microcrystalline cellulose | 80 mg |
| Sodium bicarbonate | 250 mg |
| Citric acid | 100 mg |
| Talc | 7 mg |
| Colloidal silica | 3.2 mg |
| Magnesium stearate | 6 mg |

Blood samples were collected at the following times: 0–0.5–1–1.5–2–3–4–5–6–8–10 –12–14–16–24–36–48 and 72 hours.

The samples were assayed according to a method by gas-liquid chromatography coupled to mass spectrometry with detection by mass fragmentometry.

Using the plasma values obtained, the following variables were calculated:

the area under the curve (AUC), the maximum plasma concentration ($C_{max}$), the time for obtaining the maximum plasma concentration ($T_{max}$) of acamprosate.

The relative bioavailability (F) obtained using the following equation:

$$F = \frac{\text{Dose (reference)} \times AUC(\text{tested})}{\text{dose (tested)} \times AUC(\text{reference})}$$

Results:

All the pharmacokinetic parameters observed for the mean kinetic values are presented in Table 3:

TABLE 3

Mean pharmacokinetic parameters observed after after a single oral administration of various immediate oral forms of acamprosate to 16 young healthy volunteers.

| Mean CV % | Dose mg | Tmax (h) | Cmax (ng/ml) | C24 (ng/ml) | F (%) |
|---|---|---|---|---|---|
| Reference R | 1000 | 4.3 | 248 | 60 | 100 |
| Floating tablet F | 500 | 3.4 | 278 | 28 | 121 |
| Gelatin capsule G | 500 | 1.1 | 1725 | 29 | 274 |

Conclusion:

The formulation in the form of a gelatin capsule with semisolid matrix makes it possible to obtain a larger plasma peak which indicates potentiation of the absorption which thereby causes an increase in bioavailibility by a factor of 2.74 relative to a formulation in the form of a conventional gastroresistant tablet.

What is claimed is:

1. An orally administerable galenic formulation allowing improved absorption by the transmembrane or paracellular route in the gastrointestinal tract, comprising at least one active ingredient which is a guanidine or a guanylguanidine, an absorption-promoting agent having an HLB greater than 8 which is one or more lipid substances selected from polysorbates, ethers of polyoxyethylene and alkyl, esters of polyoxyethylene and fatty acids, fatty acids, fatty alcohols, bile acids and their salts with pharmaceutically acceptable cations, esters of $C_1$–$C_6$ alkanols with fatty acids, esters of polyol with fatty acids, wherein said polyol comprises 2 to 6 hydroxyl functional groups, and polyglycolysed glycerides, and one or more pharmaceutically acceptable excipients.

2. The galenic formulation according to claim 1, further comprising an active ingredient which is hydrophilic or ionizable in physiological media which comprises at least one functional group chosen from carboxylic acid, sulphonic acid, phosphonic acid, phosphoric acid, phosphinic acid and phenol functional groups in free form or ionized form with pharmacologically acceptable cations.

3. The galenic formulation according to claim 2, wherein the active ingredient which is hydrophilic or ionizable in physiological media comprises at least one functional group chosen from sulphonic acid, phosphoric acid, phosphinic acid and phosphinic acid functional groups in free form or ionized form with pharmacologically acceptable cations.

4. The galenic formulation according to claim 1, comprising an active ingredient in the form of a calcium salt.

5. The galenic formulation according to claim 1, wherein the active ingredient, free or in ionized form with the cations or the anions present, has a solubility greater than 100 g/l.

6. The galenic formulation according to claim 5, wherein said active ingredient free or in its ionized form with the cations or the anions present has a partition coefficient D (octanol/water) corresponding to the relationship $\log_{10} D < -0.5$.

7. The galenic formulation according to claim 1, wherein an active ingredient is contained of the formula:

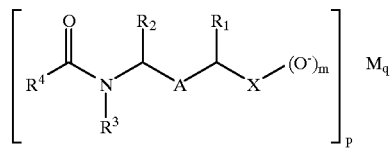

in which

X is

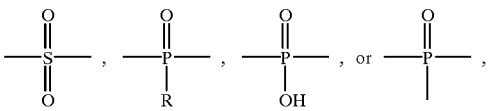

R is a $C_1$–$C_7$ alkyl radical, $R_1$, $R_2$, $R_3$ are hydrogen or a $C_1$–$C_7$ alkyl radical, A is a group of the formula:

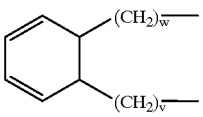

v and w=0, 1, 2, independently, or A is a group of formula

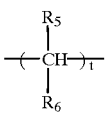

$R_5$, $R_6$, independently of each other, are hydrogen, $C_1$–$C_7$ alkyl, an aryl radical having from 6 to 14 carbon atoms, or a heteroaryl radical which furyl, thienyl or thiazolyl, it being possible for the aryl and heteroaryl radicals to carry 1 to 3 substituents which are $C_1$–$C_7$ alkyl, halogen or trifluoromethyl, and t=1–3, $R_4$ is hydrogen, $C_1$–$C_7$ alkyl, $CF_3$, aryl having from 6 to 14 carbon atoms, heteroaryl which is furyl, thienyl, or thiazolyl, it being possible for the aryl and heteroaryl radicals to carry 1 to 3 substituents which are $C_1$–$C_7$ alkyl, halogen or trifluoromethyl, M represents a monovalent metal (Na, K, Li) or a divalent metal (Ca, Mg, Sr, Zn), m=1 or 2, p=1–2 and q=1–2, p and q being such that the electrical neutrality of the salt is ensured.

8. The galenic formulation according to claim 7, wherein an active ingredient has the formula (I) in which

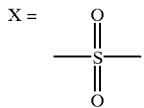

9. The galenic formulation according to claim 7, wherein an active ingredient has the formula (I) in which

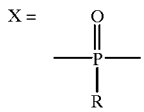

10. The galenic formulation according to claim 7, wherein an active ingredient which is hydrophilic or ionizable in physiological media of Formula I is calcium acamprosate.

11. The galenic formulation according to claim 1, wherein the active ingredient which is a guanidine or a guanylguanidine is metformin or one of its pharmaceutically acceptable salts.

12. The galenic formulation according to claim 1, wherein the absorption-promoting agent has an HLB greater than 10.

13. The galenic formulation according to claim 1, wherein the polyol esters with fatty acids are esters of glycols, esters of polyglycerols, esters or anhydrides of sorbitol.

14. The galenic formulation according to claim 1, wherein the absorption-promoting agent comprises at least one polyglycolyzed glyceride having an HLB of between 12 and 16.

15. The galenic formulation according to claim 1, wherein the absorption-promoting agent comprises at least one polyglycolyzed glyceride and a sorbitan ester with one or more fatty acids.

16. The galenic formulation according to claim 15, wherein the absorption-promoting agent comprises a mixture of one or more polyglycolyzed glycerides and a sorbitan ester with a saturated or unsaturated $C_8$–$C_{22}$ fatty acid.

17. The galenic formulation according to claim 1, wherein the weight ratio of the active ingredient to the absorption-promoting agent is between 0.001 and 10.

18. The galenic formulation according to claim 17, which is a tablet wherein the weight ratio of the active ingredient to the absorption-promoting agent is between 1 and 10.

19. The galenic formulation according to claim 17, which is a gelatin capsule wherein the weight ratio of the active ingredient to the absorption-promoting agent is between 0.1 and 2.

20. The galenic formulation according to claim 1, further comprising an agent allowing the control of the kinetics of release of the active ingredient chosen from glycerol palmitostearates, glycerol behenates, hydrogenated castor oils and mixtures thereof.

21. A method for improving the absorption by the transmembrane or paracellular route in the gastrointestinal tract of active ingredients which are hydrophilic or ionizable in physiological media, comprising administering an absorption-promoting agent in the form of an orally administerable pharmaceutical formulation according to claim 1.

22. The method according to claim 21, wherein the active ingredient which is hydrophilic or ionizable in physiological media comprises at least one functional group which is carboxylic acid, sulphonic acid, phosphinic acid, phosphoric acid, phosphinic acid or phenol functional groups in free form or ionized with pharmaceutically acceptable cations.

23. The method according to claim 21, wherein the weight ratio of the active ingredient to the absorption-promoting agent is between 0.01 and 10.

24. The method of preparing a galenic formulation according to claim 1 in the form of a tablet, comprising (i) preparing by the wet route, a granule of an active substance form a pulverulent mixture of the active substance and various excipients, and (ii) compressing, wherein the absorption-promoting agent used in (i) acts as a wetting liquid.

25. The galenic form according to claim 5, wherein the active ingredient has a solubility greater than 250 g/l.

26. The galenic form according to claim 6, wherein the active ingredient, free or in its ionized form with a cation or anion present, has a partition coefficient D (octanol/water) corresponding to the relationship $\log_{10} D < -20$.

27. The galenic form according to claim 12, wherein the absorption-promoting agent has an HLB between 12 and 16.

28. The galenic form according to claim 16, wherein the absorption-promoting agent comprises a mixture of one or more polyglycolyzed glycerides and a sorbitan ester with a saturated or unsaturated $C_{10}$–$C_{14}$ fatty acid.

* * * * *